US007233390B2

United States Patent
Chang et al.

(10) Patent No.: US 7,233,390 B2
(45) Date of Patent: Jun. 19, 2007

(54) SCATTEROMETRY FOR SAMPLES WITH NON-UNIFORM EDGES

(75) Inventors: Yia-Chung Chang, Champaign, IL (US); Hanyou Chu, San Jose, CA (US); Jon Opsal, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 416 days.

(21) Appl. No.: 10/795,915

(22) Filed: Mar. 8, 2004

(65) Prior Publication Data

US 2004/0201836 A1 Oct. 14, 2004

Related U.S. Application Data

(60) Provisional application No. 60/459,046, filed on Mar. 31, 2003.

(51) Int. Cl.
*G01N 21/00* (2006.01)
(52) U.S. Cl. .................... 356/237.1; 702/167
(58) Field of Classification Search ............ 356/237.1; 702/155, 167
See application file for complete search history.

(56) References Cited

U.S. PATENT DOCUMENTS

| 5,607,800 | A | 3/1997 | Ziger ............................. 430/8 |
| 5,739,909 | A | 4/1998 | Blayo et al. ................. 356/369 |
| 5,867,276 | A | 2/1999 | McNeil et al. ............... 356/445 |
| 5,889,593 | A | 3/1999 | Bareket ....................... 356/445 |
| 5,910,842 | A | 6/1999 | Piwonka-Corle et al. ... 356/369 |
| 5,963,329 | A | 10/1999 | Conrad et al. ............... 356/372 |
| 6,268,916 | B1 | 7/2001 | Lee et al. ..................... 356/369 |
| 6,429,943 | B1 | 8/2002 | Opsal et al. .................. 356/625 |
| 6,483,580 | B1 | 11/2002 | Xu et al. ...................... 356/300 |
| 6,867,866 | B1 * | 3/2005 | Chang et al. ................ 356/446 |
| 2001/0051856 | A1 | 12/2001 | Niu et al. ..................... 702/57 |
| 2002/0038196 | A1 * | 3/2002 | Johnson et al. ............ 702/179 |

(Continued)

FOREIGN PATENT DOCUMENTS

WO WO 03/009063 1/2003

(Continued)

OTHER PUBLICATIONS

Bischoff et al., "Characterization of 3D resist patterns by means of optical scatterometry", May 1999, SPIE, vol. 3743, pp. 49-60.*

(Continued)

*Primary Examiner*—Gregory J. Toatley, Jr.
*Assistant Examiner*—Kara Geisel
(74) *Attorney, Agent, or Firm*—Stallman & Pollock LLP

(57) ABSTRACT

A method for simulating the optical properties of samples having non-uniform line edges includes creating a model for the sample being analyzed. To simulate roughness, lines within the model are represented as combinations of three dimensional objects, such as circular or elliptical mesas. The three-dimensional objects are arranged in a partially overlapping linear fashion. The objects, when spaced closely together resemble a line with edge roughness that corresponds to the object size and pitch. A second method allows lines within the model to vary in width over their lengths. The model is evaluated using a suitable three-dimensional technique to simulate the optical properties of the sample being analyzed.

27 Claims, 4 Drawing Sheets

U.S. PATENT DOCUMENTS

| | | | |
|---|---|---|---|
| 2002/0158193 A1 | 10/2002 | Sezginer et al. | 250/237 |
| 2003/0147086 A1 | 8/2003 | Rosencwaig et al. | 356/601 |
| 2004/0070772 A1* | 4/2004 | Shchegrov et al. | 356/625 |
| 2005/0280810 A1* | 12/2005 | Johnson | 356/237.5 |

FOREIGN PATENT DOCUMENTS

WO      WO 03/075041 A2      9/2003

OTHER PUBLICATIONS

Yeung et al., "Electromagnetic Scatterometry Applied to In Situ Metrology", 2001, SPIE, vol. 4344, pp. 484-495.*

J. Opsal et al., "Contact hole inspection by real-time optical CD metrology", Metrology, Inspection, and Process Control for Microlithography XVII, Daniel J. Herr, Editor, Proceedings of SPIE vol. 5038 (2003), pp. 597-603.

J. Bischoff et al., "Optical Digital Profilometry applications on contact holes", Metrology, Inspection, and Process Control for Microlithography XVII, Daniel J. Herr, Editor, Proceedings of SPIE vol. 5038 (2003), pp. 1080-1088.

B.D. Bunday et al., "CD-SEM Measurement of Line Edge Roughness Test Patterns for 193 nm Lithography", Metrology, Inspection, and Process Control for Microlithography XVII, Daniel J. Herr, Editor, Proceedings of SPIE vol. 5038 (2003), pp. 674-688.

* cited by examiner

702a

702b 702a
702b

SCATTEROMETRY FOR SAMPLES WITH NON-UNIFORM EDGES

PRIORITY CLAIM

The present application claims priority to U.S. Provisional Patent Application Ser. No. 60/459,046, filed Mar. 31, 2003, the disclosure of which is incorporated in this document by reference.

TECHNICAL FIELD

The present invention relates generally to optical methods for inspecting and analyzing semiconductor wafers and other samples. In particular, the present invention relates to the use of scatterometry to analyze samples that have non-uniform edges.

BACKGROUND OF THE INVENTION

As semiconductor geometries continue to shrink, manufacturers have increasingly turned to optical techniques to perform non-destructive inspection and analysis of semiconductor wafers. Techniques of this type, known generally as optical metrology, operate by illuminating a sample with an incident field (typically referred to as a probe beam) and then detecting and analyzing the reflected energy. Ellipsometry and reflectometry are two examples of commonly used optical techniques. For the specific case of ellipsometry, changes in the polarization state of the probe beam are analyzed. Reflectometry is similar, except that changes in intensity are analyzed. Ellipsometry and reflectometry are effective methods for measuring a wide range of attributes including information about thickness, crystallinity, composition and refractive index. The structural details of various metrology devices are more fully described in U.S. Pat. Nos. 5,910,842 and 5,798,837 both of which are incorporated in this document by reference.

As shown in FIG. 1, a typical ellipsometer or reflectometer includes an illumination source that creates a mono or polychromatic probe beam. The probe beam is focused by one or more lenses to create an illumination spot on the surface of the sample under test. A second lens (or lenses) images the illumination spot (or a portion of the illumination spot) to a detector. The detector captures (or otherwise processes) the received image. A processor analyzes the data collected by the detector.

Scatterometry is a specific type of optical metrology that is used when the structural geometry of a sample creates diffraction (optical scattering) of the incoming probe beam. Scatterometry systems analyze diffraction to deduce details of the structures that cause the diffraction to occur. Various optical techniques have been used to perform optical scatterometry. These include broadband spectroscopy (U.S. Pat. Nos. 5,607,800; 5,867,276 and 5,963,329), spectral ellipsometry (U.S. Pat. No. 5,739,909) single-wavelength optical scattering (U.S. Pat. No. 5,889,593), and spectral and single-wavelength beam profile reflectance and beam profile ellipsometry (U.S. Pat. No. 6,429,943). Scatterometry in these cases generally refers to optical responses in the form of diffraction orders produced by periodic structures, that is, gratings on the wafer. In addition, it may be possible to employ any of these measurement technologies, e.g., single-wavelength laser BPR or BPE, to obtain critical dimension (CD) measurements on non-periodic structures, such as isolated lines or isolated vias and mesas. The above cited patents and patent applications, along with PCT Application WO 03/009063, U.S. Application 2002/0158193, U.S. Application 2003/0147086, U.S. Application 2001/0051856 A1, PCT Application WO 01/55669 and PCT Application WO 01/97280 are all incorporated herein by reference.

To analyze diffraction, scatterometry systems use a modeling process. The modeling process is based on a parametric model of the particular sample being analyzed. The model is evaluated to predict the empirical measurements that a scatterometer will record for the sample. The predicted measurements and the empirical measurements are compared to determine if the model matches the empirical results. The model is then perturbed and re-evaluated until the predicted results and empirical results match within a desired goodness of fit. At that point, the parametric model is assumed to match the sample being analyzed.

As shown in FIG. 2, a typical scatterometry sample includes a scattering structure formed on a substrate. For the specific example of FIG. 2, the scattering structure is a grating composed of a series of individual lines. In general, the scattering structure may be periodic (as in the case of FIG. 2) or isolated. Isolated structures include, for example, individual lines or individual vias. The scattering structure of FIG. 2 is uniform (i.e., exhibits translational symmetry) along the Y axis. For this reason, this particular scattering structure is considered to be two-dimensional. Three dimensional scattering structures are also possible both in isolation (e.g., single via) or periodically (e.g., pattern of vias). The scatting structure is covered by an incident medium that is typically air but may be vacuum, gas, liquid, or solid (such as an overlaying layer or layers). One or more layers may be positioned between the scattering structure and the substrate. During analysis, a probe beam is directed at the scattering structure. For most applications, the probe beam intersects the scattering structure at a normal angle—it is perpendicular to the lines from which the scattering structure is formed. It is also possible to use a non-normal angle. This is referred to as conical scattering.

In practice, it is not generally possible to construct semiconductor wafers with the degree of orthogonality shown in FIG. 2. This is due to a number of physical limitations, such as the accuracy of the equipment used during fabrication. The overall result is that the scattering structures typically included in semiconductor wafers tend to have sloping instead of vertical walls, rounded corners at the foot and top of lines and a range of other artifacts introduced during the fabrication process. As semiconductor features continue to shrink, molecular size introduces a second type of non-orthogonality into the fabrication process. This second type of non-orthogonality arises because the molecules used to form the features of semiconductors become increasingly large (in a relative sense) as the features become increasingly small. As a result, small features tend to exhibit a non-uniformity, or roughness, caused by the physical size of their constituent molecules. This is particularly true where organic photo-resists are used. FIG. 3 shows a specific example where the use of relatively large molecules has resulted in line edge roughness.

Non-uniformity, or roughness of the type shown in FIG. 3, changes the measurements recorded during the scatterometry process. This is problematic because the models used to predict the empirical scatterometry measurements are not designed in a way that predicts the type of measurements that are associated with rough edges or other non-uniformities. For many modeling techniques, this problem is exacerbated because they assume that the scattering sample is two-dimensional (as is the case for the sample of FIG. 2).

For these reasons and others, a need exists for scatterometry techniques that are compatible with samples having rough or non-uniform edges. This need is particularly apparent for high density semiconductor wafers where feature sizes are small and particularly apparent where organic photo-resists are used.

SUMMARY OF THE INVENTION

The present invention provides a method for simulating line edge roughness within optical models of scatterometry samples. For typical applications, the sample is a semiconductor wafer and includes a scattering structure formed on one or more underlying layers. The lowermost of the underlying layers is commonly referred to as a substrate. The scatting structure is covered by an incident medium that is typically air but may be vacuum, gas, liquid, or solid (such as an overlaying layer or layers). In the most typical case, the scattering structure is a grating consisting of a periodic series of lines. By appropriate generalizations, other isolated or periodic features may also be modeled.

To model roughness, lines within the scattering structure are represented as combinations of three dimensional objects. A line, for example, can be modeled as a linear series of cylindrical mesas. The mesas, when spaced closely together (spacing is also described as pitch) resemble a line with an edge roughness that corresponds to the mesa size and pitch. By controlling mesa size and pitch, the roughness of many line edges may be effectively modeled. By including multiple series of mesas with differing sizes and pitches, arbitrary edge roughness can be modeled. This is somewhat analogous to combining different sine waves to construct arbitrary waveforms. It should also be noted that the number of mesas required may be reduced (for many types of edge roughness) by using elliptically shaped mesas, oriented in parallel with the line being modeled.

Another, related method for modeling edge roughness is to construct lines within the scattering structure to have variable cross-section. By changing the cross-section as a function of line position, arbitrary edge roughness may be modeled.

DETAILED DESCRIPTION OF THE PREFERRED EMBODIMENTS

The present invention provides a method for simulating line edge roughness within optical models of scatterometry samples. For typical applications, the sample is a semiconductor wafer and includes a scattering structure formed on one or more underlying layers. The lowermost of the underlying layers is commonly referred to as a substrate. The scatting structure is covered by an incident medium that is typically air but may be vacuum, gas, liquid, or solid (such as an overlaying layer or layers). In the most typical case, the scattering structure is a grating consisting of a periodic series of lines. By appropriate generalizations, other isolated or periodic features may also be modeled.

Figure 4A:
FIGS. 4A through 4C are block diagrams showing a line with edge roughness modeled using three dimensional mesas.
Figure 4B:

To model roughness, edges within the scattering structure are represented as combinations of three dimensional objects. This is shown, for example, in FIG. 4A where a line is modeled using a series of cylindrical mesas. Each shape (mesa) has the same size and the series of shapes are aligned to define the edge of a line. The shapes are separated by a predetermined distance (pitch). As shown in FIG. 4B, decreasing the linear separation between mesas (i.e., using more mesas per unit distance along the line) changes the texture of the line model. The overall size of the mesas (e.g., their diameter) may be varied to control line width and roughness.

Figure 4C:
Figure 5:
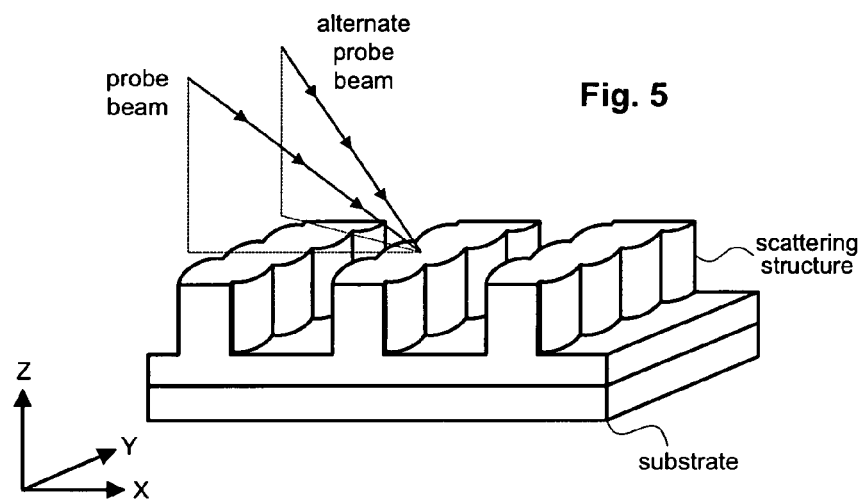
FIG. 5 is a perspective drawing of a sample exhibiting line edge roughness modeled using three dimensional mesas.

In FIG. 4C, the cylindrical mesas are replaced with elliptical mesas. The use of the elliptical cross section reduces the number of thee-dimensional objects required to model a given line. The use of ellipses also increases the types of roughness that may be modeled, since the dimensions of the ellipse (major axis, minor axis) are variable. A sample model using a combination of elliptical shaped mesas is shown in FIG. 5.

Figure 6:
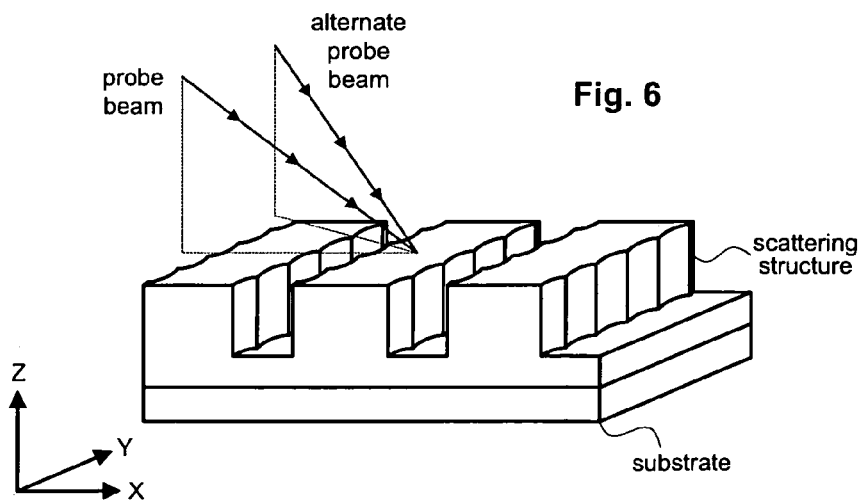
FIG. 6 is a perspective drawing of a sample exhibiting line edge roughness modeled using three dimensional voids.

It should be noted that circular and elliptical mesas are merely examples of three dimensional objects that may be used for the modeling method. Mesas may be defined to have any desired cross section (e.g., oval, triangular or square). Mesas may also be defined conically to have sloping sides. This can be used to model lines that have sloping sidewalls. It is also possible to model lines using combinations of voids. A specific example of this is shown in FIG. 6 where a sample is shown to include a series of trenches. Each trench is modeled as a linear series of overlapping elliptically shaped holes. The samples of FIGS. 5 and 6 are, in this respect, conjugate halves, with the solids used to model the sample of FIG. 5 replaced with voids for the sample of FIG. 6. Holes can have any desired cross-section and maybe be constructed conically to represent lines with sloping sidewalls.

Figure 7A:
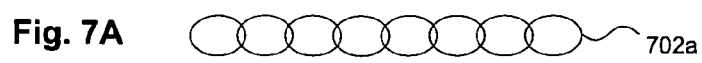
FIG. 7A shows a first series of three dimensional objects.
Figure 7B:
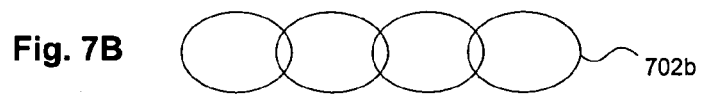
FIG. 7B shows a second series of three dimensional objects.

As shown in FIGS. 7A through 7D, it is possible to combine multiple series of three-dimensional shapes to model complex line edges. FIGS. 7A shows a first series of elliptical mesas (or holes) 702a and FIGS. 7B shows a second series of elliptical mesas (or holes) 702b. The mesas in series 702b are approximately twice as large as the mesas in series 702a. The mesas in series 702b are spaced with half the frequency of the mesas in series 702a (i.e., the pitch of series 702*b* is half of the pitch of series 702*a*). The two series start at the same position (i.e., the have the same relative phase).

Figure 7C:
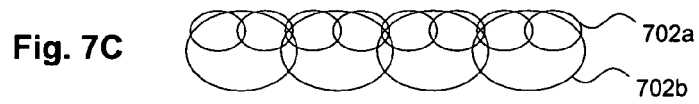
FIG. 7C shows the series of FIG. 7A superimposed on the series of FIG. 7B.
Figure 7D:
FIG. 7D shows a line edge modeled using the superimposition of FIG. 7C.

FIG. 7C shows a superposition of the two separate series 702. For this particular example, the series of smaller mesas (702*a*) has been aligned to coincide with the upper edge of the larger series (702*b*). The shape resulting from this superposition is shown in FIG. 7D. As shown, the upper edge of the resulting shape has an attenuated arc-like shape attributable to the addition of the smaller mesas. The lower edge of the resulting shape retains the arc-like nature of the series of larger mesas.

FIGS. 7A through 7D are intended to demonstrate that multiple series of three dimensional objects may be combined to represent arbitrary line edge roughness. Typically, where multiple series are used, each series will be different in some respect. The differences may be in terms of shape size (as is the case for series 702*a* and 702*b*) shape pitch (once again, demonstrated by series 702*a* and 702*b*) or shape offset (relative phase) or various combinations thereof which can be used to represent arbitrary line edge roughness. Combinations of this type may be used to define asymmetric lines of the type shown in FIG. 7D where opposing edges have different roughness.

The preceding paragraphs describe the modeling of line edge roughness using collections of three dimensional solids and voids. A second technique models each line as a single three dimensional object. In terms of the coordinate system of FIG. 5 and 6, each line is modeled to have a specific X-Z profile. Typically, this means that each line has a defined cross-section that is rectangular, trapezoidal or other symmetric or asymmetric shape. That shape is allowed to vary along the Y axis. This means that each line can increase or decrease in width or vary the shape of its profile as a function of position along the Y axis. In effect, each line can have a different cross-sectional shape for each Y location.

Figure 8A:
FIG. 8A though 8C show periodic functions of different frequencies.
Figure 8B:
FIG. 8D shows a line edge modeled using the periodic functions of FIG. 8A though 8C.
Figure 8C:
Figure 8D:
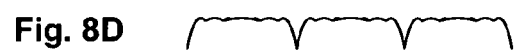
Figure 9A:
FIG. 9A though 9C show periodic functions of different frequencies.
Figure 9B:
FIG. 9D shows a line edge modeled using the periodic functions of FIG. 9A though 9C.
Figure 9C:
Figure 9D:

To define line profile as a function of position, one or more periodic functions may be used. In combination, the periodic function can be used to represent arbitrary line edge roughness. This is shown, for example, in FIGS. 8A through 8D. The first three of these FIGS. (8*a*-8*c*) show different periodic functions for a single line edge. FIG. 8D shows the combination of the three separate edge functions to generate an arbitrary edge. The combination of periodic shapes can be modified, amplified or reduced as a function of Z to further increase the type of edge roughness or non-uniformity that can be modeled. In general, it is possible to model any desired edge profile as a Fourier decomposition of periodic functions. As an example, FIG. 9A shows a sine function of a given frequency and amplitude. FIGS. 9B and 9C show odd harmonics of the sine function of FIG. 9A. The combination of these three functions results in the square wave line edge of FIG. 9D. Fourier decomposition may be used to model edge profiles that have a repeating pattern (as in FIG. 9D) as well as non-repeating edge profiles.

Scattering structure models may be constructed using any of the techniques described in the preceding sections. Once constructed, the models may be evaluated using any appropriate three-dimensional approach. Two particularly appropriate approaches are described in the co-pending U.S. patent application Ser. Nos. 10/212,385, and 10/345,814. Those disclosures are incorporated in this document by reference. See also: "Contact hole inspection by real-time optical CD metrology," Opsal, et al. SPIE Microlithography 2003, pages 5038-63 and "Optical digital profilometry applications on contact holes," Bischoff et al, Metrology, Inspection, and Process Control for Microlithography XVII, Proc. of SPIE Vol. 5038, pp. 1080-1088, 2003, both incorporated herein by reference.

Figure 1:
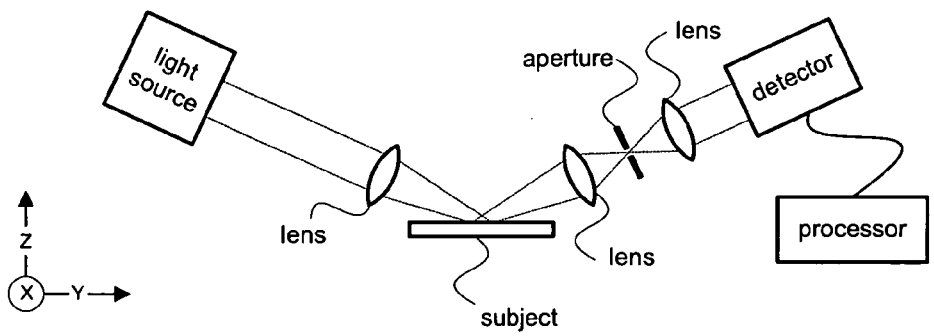
FIG. 1 is a diagram of a prior art optical metrology system.
Figure 2:
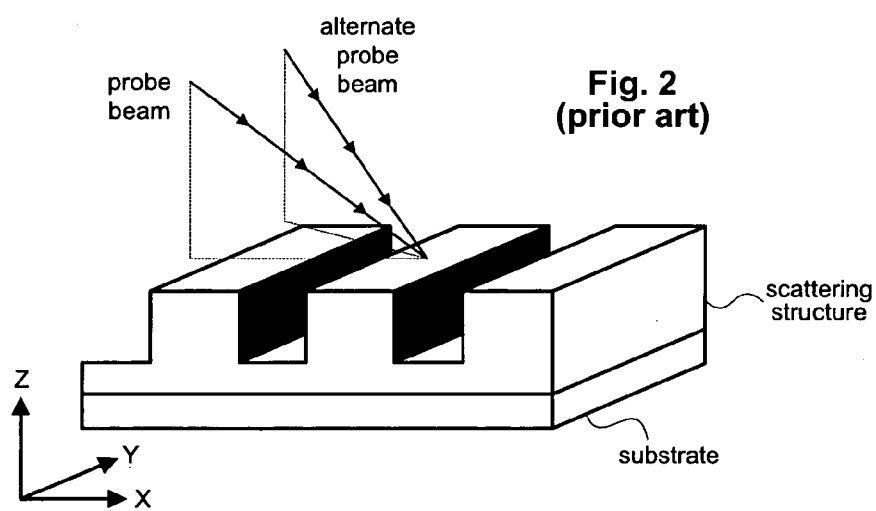
FIG. 2 is a perspective drawing of a typical scatterometry sample.
Figure 3:
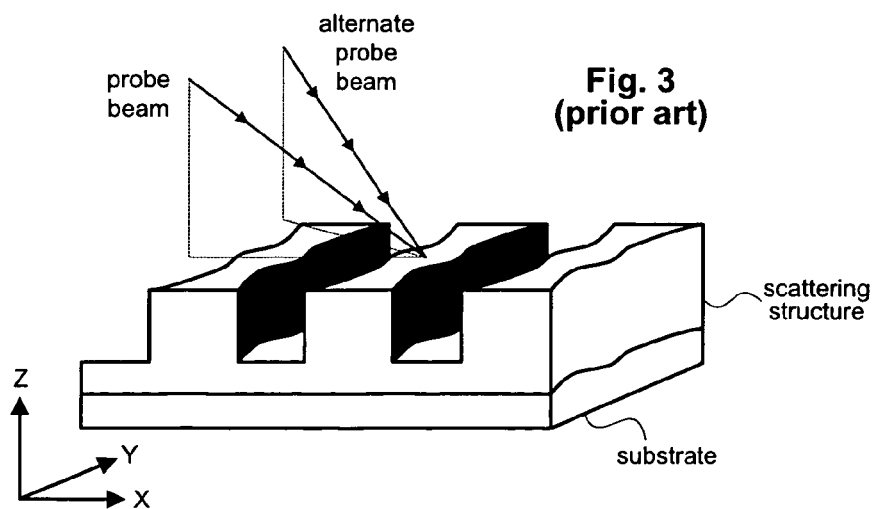
FIG. 3 is a perspective drawing of a typical sample exhibiting line edge roughness.

In use, a sample is optically inspected using any of the conventional optical inspection techniques discussed above and represented generically by FIG. 1. In the preferred embodiment, a spectroscopic reflectometer or spectroscopic ellipsometer (or a combination of both) is used to generate measurement signals as a function of wavelength. These signals are compared to theoretical signals which are generated based on the model of the subject invention. The theoretical signals could be generated in the form of sets of data in a database representing a range of different sample parameters. Alternatively, the parameters of the model can be iteratively modified in order to minimize the differences between the measured signals and the theoretical data.

What is claimed is:

1. A method for optically inspecting a sample having at least one longitudinally extending line, the method comprising:
   illuminating the sample with a probe beam;
   measuring the diffraction resulting from the interaction of the probe beam and the sample;
   defining a model of the sample, the model including a first series of three-dimensional shapes that define a longitudinal edge of a line within the sample;
   evaluating the model in three dimensions to predict the diffraction resulting from the interaction of the probe beam and the sample;
   adjusting and reevaluating the model to minimize the difference between the predicted and measured data to derive information about the roughness of the edge; and
   storing the derived roughness information for subsequent use.

2. A method as recited in claim 1, in which the three-dimensional shapes represent mesas on the surface of the sample.

3. A method as recited in claim 2, in which the mesas are shaped as cylindrical or conical projections from the sample surface with the projections having circular or elliptical cross-sections.

4. A method as recited in claim 1, in which the three-dimensional shapes represent holes in the surface of the sample.

5. A method as recited in claim 4, in which the holes are shaped as cylindrical or conical voids in the sample surface with the voids having circular or elliptical cross-sections.

6. A method as recited in claim 1, in which the model includes a second series of three-dimensional shapes that refines the definition of the line edge within the sample.

7. A method as recited in claim 6, in which the first series and second series of three-dimensional shapes differ in shape size, pitch or phase.

8. A method of evaluating the roughness of a line edge on a wafer comprising the steps of:
   obtaining optical measurement data from the wafer;
   comparing the measured data to calculated data, the calculated data based on a model that includes the scattering effects from an array of holes or mesas and wherein the spacing between the holes or mesas in the models is selected so that the holes or mesas overlap to approximate an undulating edge;
   adjusting the model to minimize the difference between the calculated and measured data to derive information about the roughness of the edge; and
   storing the derived roughness information for subsequent use.

9. A method as recited in claim 8, in which the mesas are shaped as cylindrical or conical projections from the sample surface with the projections having circular or elliptical cross-sections.

10. A method as recited in claim 8, in which the holes are shaped as cylindrical or conical voids in the sample surface with the voids having circular or elliptical cross-sections.

11. A method as recited in claim 8, in which the array of holes or mesas includes a first series of holes or mesas and a second series of holes or mesas in which the first series and second series differ size, pitch or phase of the mesas or holes.

12. A method for optically inspecting a sample having at least one longitudinally extending line, the method comprising:
    illuminating the sample with a probe beam;
    measuring the diffraction resulting from the interaction of the probe beam and the sample;
    defining a model of the sample, the model including at least one line having a width defined to vary over the longitudinal length of the line;
    evaluating the model in three dimensions to predict the diffraction resulting from the interaction of the probe beam and the sample;
    adjusting and reevaluating the model to minimize the difference between the predicted and measured data to derive information about the roughness of the edge; and
    storing the derived roughness information for subsequent use.

13. A method as recited in claim 12, in which the line width is defined in terms of one or more periodic functions.

14. A method as recited in claim 13, in which the periodic functions differ in amplitude, frequency or phase.

15. An apparatus for evaluating a-wafer having one or more longitudinally extending lines formed on the surface thereof comprising:
    a light source for generating a probe beam;
    a detector for detecting light from the probe beam diffracted from the wafer and generating measurement signals; and
    a processor which compares the measurement signals to theoretical data, said theoretical data being generated using a model of the sample, said model including a representation of a line having roughness along a longitudinal edge, said representation being based on a series of overlapping three-dimensional geometrical features.

16. An apparatus as recited in claim 15, wherein the measurement signals are compared to a data base of theoretical data generated using a parametized model.

17. An apparatus as recited in claim 15, wherein said processor iteratively adjusts the model so that the differences between the theoretical data and the measurement signals are minimized.

18. An apparatus as recited in claim 15, wherein said light source is broadband and the detection means generates measurement signals as a function of wavelength.

19. An apparatus as recited in claim 18, wherein the apparatus includes a spectrometer.

20. An apparatus as recited in claim 18, wherein the apparatus includes an ellipsometer.

21. An apparatus as recited in claim 15, in which the three-dimensional features represent mesas on the surface of the wafer.

22. An apparatus as recited in claim 21, in which the mesas are shaped as cylindrical or conical projections from the sample surface with the projections having circular or elliptical cross-sections.

23. An apparatus as recited in claim 15, in which the three-dimensional features represent holes in the surface of the sample.

24. An apparatus as recited in claim 21, in which the holes are shaped as cylindrical or conical voids in the sample surface with the voids having circular or elliptical cross-sections.

25. An apparatus for evaluating a wafer having one or more longitudinally extending lines formed on the surface thereof comprising:
    a light source for generating a probe beam;
    a detector for detecting light from the probe beam diffracted from the wafer and generating measurement signals; and
    a processor which compares the measurement signals to theoretical data, said theoretical data being generated using a model of the sample, said model including a representation of a line having roughness along a longitudinal edge, said representation being based on a line having a width which varies over the length thereof and being defined by a superposition of periodic functions.

26. A method for optically inspecting a sample, the method comprising:
    illuminating the sample with a probe beam;
    measuring the diffraction resulting from the interaction of the probe beam and the sample;
    defining a model of the sample, the model including a first series of three-dimensional shapes that define the edge of a line within the sample and a second series of three-dimensional shapes that refines the definition of the line edge within the sample;
    evaluating the model in three dimensions to predict the diffraction resulting from the interaction of the probe beam and the sample;
    adjusting and reevaluating the model to minimize the difference between the predicted and measured data to derive information about the roughness of the edge; and
    storing the derived roughness information for subsequent use.

27. A method for optically inspecting a sample, the method comprising:
    illuminating the sample with a probe beam;
    measuring the diffraction resulting from the interaction of the probe beam and the sample;
    defining a model of the sample, the model including at least one line having a width defined to vary over the length of the line and wherein the line width is defined in terms of one or more periodic functions;
    evaluating the model in three dimensions to predict the diffraction resulting from the interaction of the probe beam and the sample;
    adjusting and reevaluating the model to minimize the difference between the predicted and measured data to derive information about the roughness of the edge; and
    storing the derived roughness information for subsequent use.

* * * * *